(12) United States Patent
Yamazaki et al.

(10) Patent No.: US 9,161,881 B2
(45) Date of Patent: Oct. 20, 2015

(54) TAPPING DEVICE FOR PRODUCING BEAUTIFUL SKIN

(75) Inventors: Iwao Yamazaki, Tokyo (JP); Kazunori Yamanaka, Tokyo (JP)

(73) Assignee: YA-MAN LTD., Tokyo (JP)

( * ) Notice: Subject to any disclaimer, the term of this patent is extended or adjusted under 35 U.S.C. 154(b) by 618 days.

(21) Appl. No.: 13/509,148

(22) PCT Filed: Nov. 21, 2011

(86) PCT No.: PCT/JP2011/076776
§ 371 (c)(1),
(2), (4) Date: May 10, 2012

(87) PCT Pub. No.: WO2012/086351
PCT Pub. Date: Jun. 28, 2012

(65) Prior Publication Data
US 2012/0253246 A1    Oct. 4, 2012

(30) Foreign Application Priority Data
Dec. 24, 2010  (JP) ................................. 2010-287940

(51) Int. Cl.
*A61H 23/00*     (2006.01)
*A61H 39/04*     (2006.01)
*A61N 1/30*      (2006.01)
*A61N 1/04*      (2006.01)

(52) U.S. Cl.
CPC .............. *A61H 23/006* (2013.01); *A61H 39/04* (2013.01); *A61H 2201/1215* (2013.01); *A61H 2201/149* (2013.01); *A61H 2201/1664* (2013.01); *A61H2201/1685* (2013.01); *A61H 2201/5043* (2013.01); *A61N 1/0428* (2013.01); *A61N 1/303* (2013.01)

(58) Field of Classification Search
CPC ..... A61H 39/04; A61H 23/00; A61H 23/006; A61H 2201/1215; A61H 2201/1685; A61H 2201/5043; A61H 2201/149; A61H 2201/1664; A61N 1/303; A61N 1/0428
USPC ........... 601/15, 18, 21, 84, 89, 92, 93, 94, 95, 601/97, 101, 103, 107, 108, 111, 134, 135, 601/136, 137, 138; 606/237, 238, 239
See application file for complete search history.

(56) References Cited

U.S. PATENT DOCUMENTS

| | | | |
|---|---|---|---|
| 4,549,535 A * | 10/1985 | Wing | 601/108 |
| 6,228,042 B1 * | 5/2001 | Dungan | 601/107 |
| 7,083,580 B2 * | 8/2006 | Bernabei | 601/15 |

FOREIGN PATENT DOCUMENTS

| | | |
|---|---|---|
| JP | 2005-328900 | 12/2005 |
| JP | 2007-29518 | 2/2007 |
| JP | 2007-029518 | 2/2007 |

OTHER PUBLICATIONS

Microfilm of the specification and drawings annexed to the request of Japanese Utility Model No. 133073/1980 (Laid Open No. 58465/1982) dated Apr. 6, 1982 (3 pages total).

*Primary Examiner* — Quang D Thanh
(74) *Attorney, Agent, or Firm* — Hamre, Schumann, Mueller & Larson, P.C.

(57) ABSTRACT

In the tapping device for producing beautiful skin, a Head contacts with skin. A Tapping mechanism pats the skin facing the Head with a Pad. The Tapping mechanism is equipped with the Pad at one end, and has a Shaft from which the Head projects and rolls back by piston actions. A Biasing member biases the Shaft toward one side of the piston actions. A Wire rod empowers the Shaft towards the direction resisting the biasing power of the Biasing member when tension is provided. An Actuator provides tension intermittently in a Wire rod, the tension of the wire rod and biasing of the bias member providing piston actions.

5 Claims, 12 Drawing Sheets

(a)

(b)

(a)

(b)

(a)

(a)

(b)

(c)

TAPPING DEVICE FOR PRODUCING BEAUTIFUL SKIN

TECHNICAL FIELD

The present invention relates to a device for producing beautiful skin, which taps a face or arms.

BACKGROUND ART

Tapping is a simple skin-care technique producing a rhythmical vibration in skin by patting repeatedly with fingers. Besides beneficial effects of massage, it is said to be effective in relaxation and stimulating an acupuncture point. This technique is generally included in service at aesthetic salons.

Additional, there are some handy devices for producing beautiful skin that practice tapping like this. For example, a device disclosed in Patent Document 1 (particularly p. 5-7, FIG. 4-6) fixes up an iontophoresis electrode and a tapping mechanism with a pad. They are provided for helping active ingredients in essence to infiltrate into skin by introducing ions with an iontophoresis electrode and by patting skin with a pad of a tapping mechanism.

This device for producing beautiful skin is composed of a tapping mechanism with a shaft whose head projects and rolls back a pad from a contact face with skin, a biasing member that biases the shaft, a cam follower fixed to the shaft, and a motor-driven twist cam controlling the shaft's piston action resisting biasing power of biasing member engaging the cam follower.

PRIOR ART PATENT DOCUMENT

Patent Document 1: Japanese Patent Application Publication No. 2007-029518

SUMMARY OF THE INVENTION

The present invention is made to enable a tapping mechanism to become more tranquil, smaller, and lighter, on purpose to provide a handier device for producing beautiful skin.

The present device for producing beautiful skin includes a head to contact with skin, and is equipped with a tapping mechanism for patting skin facing this head with the pad, the tapping mechanism is equipped with the pad at one end, having a shaft wherein the head projects and rolls back the pad by piston actions, a biasing member that biases the shaft towards one side of the piston actions, a wire rod that empowers the shaft towards the direction resisting the biasing power of the biasing member when tension is provided, and an actuator that provides tension intermittently in this wire rod.

The shaft of the tapping mechanism allows for back and forth actions by tension of a wire rod, which is different from the conventional way using a cam. It is effective to eliminate frictional noises and silent. Also, it is quite flexible in terms of shape, and possible to obtain strokes using only a narrow space and to make a tapping mechanism smaller and lighter, and to provide a handy device for producing beautiful skin.

The device further features that the above-mentioned head is equipped with an electrode for infiltrating essence by introducing ions. The electrode for infiltrating essence into the skin, is available concurrently with tapping, and it is good for enhancing effectiveness of skin care by encouraging essence to infiltrate.

The device also further features that the above-mentioned tapping mechanism has a space between the surface of the head and the pad's backward position. As the tapping mechanism has a space between the surface of the head and the pad's backward position, it becomes possible to give momentum to a pop-up pad, and to tap powerfully.

The device still further features that the above-mentioned tapping mechanism is equipped with more than two exchangeable pads which are different in dimension, and composed on one side of the shaft for freely being put on and taken off. As the tapping mechanism has more than two exchangeable pads which are different in dimension, and composed on one side of the shaft for freely being put on and taken off, it becomes possible to modify dimensions of the pads according to user applications or preferences.

The device also features that the above-mentioned tapping mechanism is composed of a pad whose surface is a concavely curved cupule. As the surface of pads is concavely curved and it works as a cupule, pads are not only for patting but also pulling skin by suction, which stimulates skin and facilitates the blood circulation.

DETAILED DESCRIPTION OF THE INVENTION

Hereinafter, the present invention will be concretely described with reference to the drawings.

Figure 1:
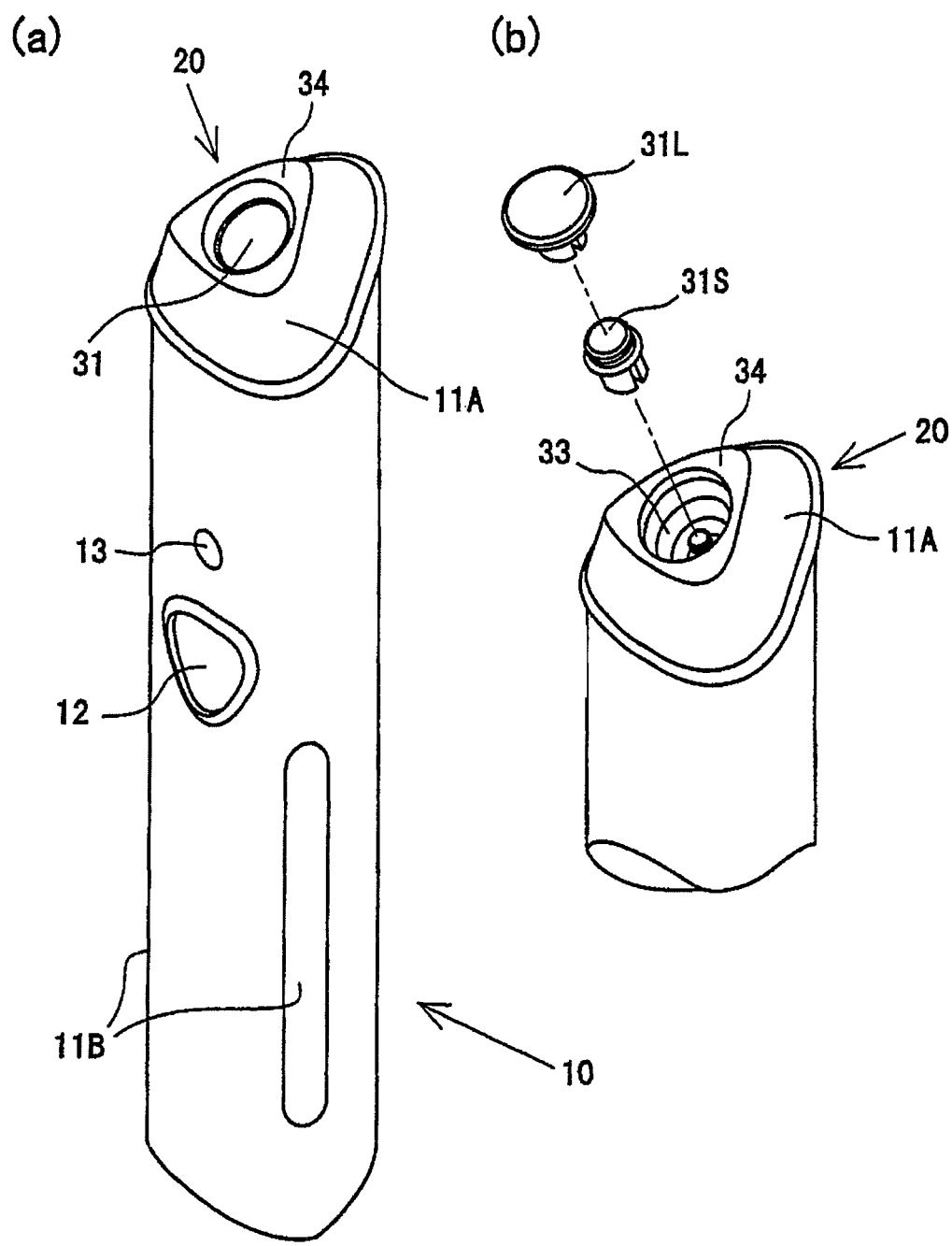
FIG. 1 is a perspective view of a device for producing beautiful skin according to an Embodiment of the present invention.
 (a) shows an appearance of the whole device, while
 (b) shows explodedly a substantial part.

In FIG. 1, item 10 is a handle for a user to grip, 20 is a head that operates introduction of ions and tapping.

11A. 11B are electrodes for introducing ions: 11A is an electrode placed at Head 20 for contacting with skin, and 11B is an electrode placed at Handle 10 for contacting with padded palms.

Item 12 is an operating button to adjust the master electrical switch when turned on/off and the strength of the tapping, 13 is a display whose lighting is turned on and off according to the operating state. Each is fitted with Handle 10.

Further, as to Head 20 in FIGS. 1. 31L and 31S are pads to pat skin, 31L indicates the wider, while 31S is the narrower. They are exchangeably fixed according to user preferences.

Figure 2:
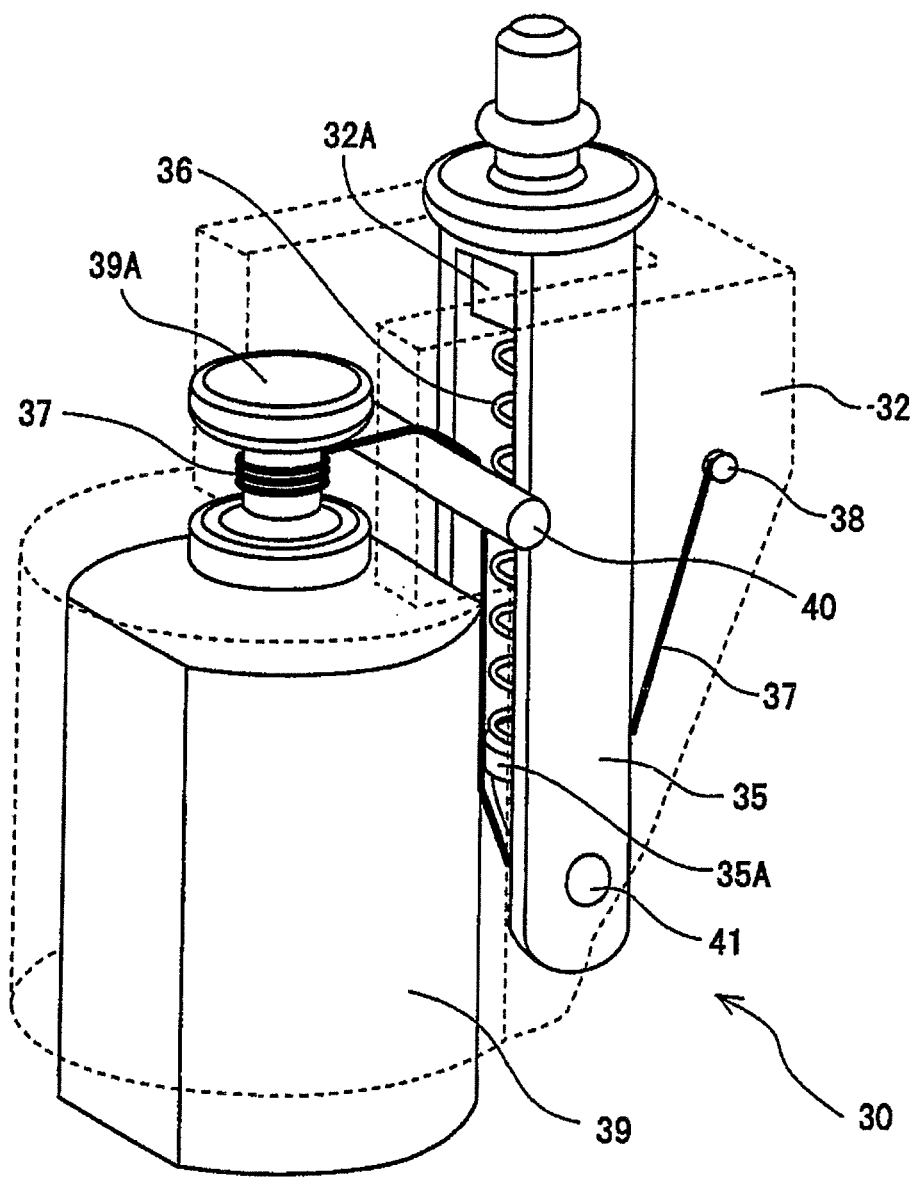
FIG. 2 is an enlarged perspective view of the substantial part of the device in FIG. 1 and it shows a state that a pad is detached.
Figure 3:
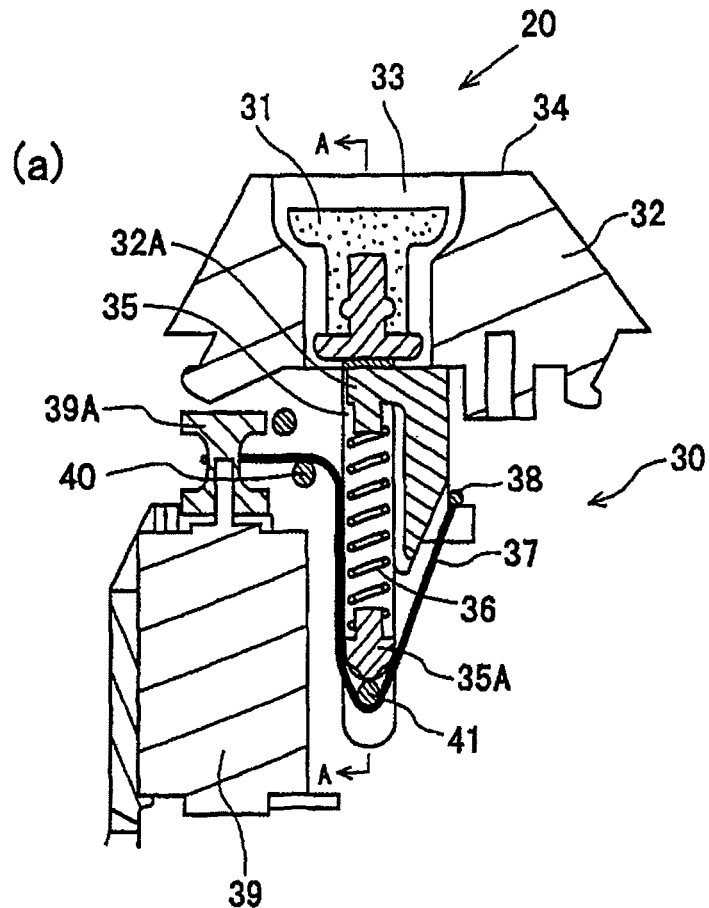
FIG. 3 is a cross-section view of FIG. 2,
 (a) shows a state that a pad falls back, while
 (b) shows a cross-section surface of the substantial part along A-A line in (a).
Figure 3:
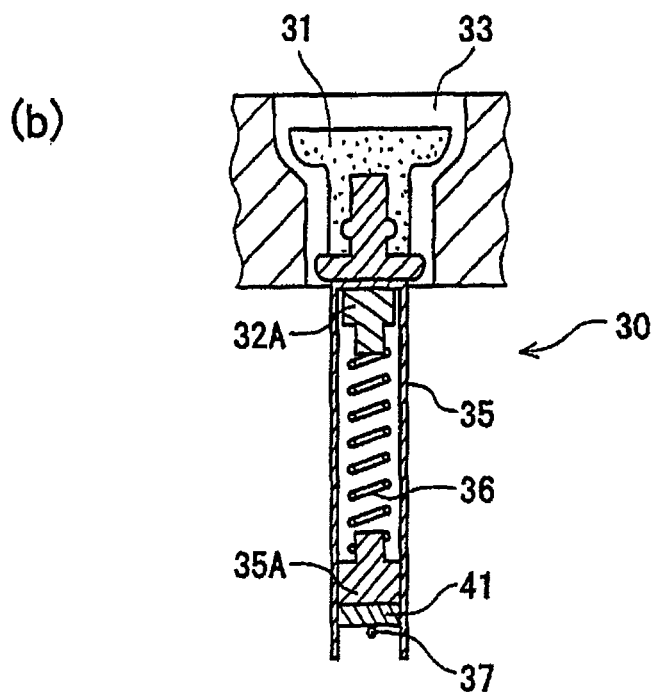

In FIGS. 2 and 3, 30 is a tapping mechanism, 32 is a frame of Tapping mechanism 30, 33 is an air pocket in Frame 32, 34 is a contact face of Handle 20 facing skin, 35 is a shaft equipped with Pad 31 on one end, Pad 31 projects out from Head 20's Contact face 34 or rolls back to the inside of Air pocket 33 by piston actions.

Additionally, 36 is a biasing member such as a coil spring that biases Shaft 35 to downward direction of piston actions, which is installed between Base 35A of Shaft 35 and Locking part 32A integrated with Frame 32.

37 is a wire rod pressing Shaft 35 to advancing direction that resists biasing power of Biasing member 36 when tensioned, 38 is a fixed member such as a pin to fix one end of Wire rod 37, 39 is an actuator such as a motor intermittently providing tension to Wire rod 37, 39A is a take-up axis such as a pin placed to sandwich Shaft 35 with Fixed member 38, 40 and 41 are pilot pins. Further, Pilot pin 41 is integrally attached to Shaft 35. The position of Fixed member 38 is closer to Contact face 34 than to Take-up axis 39, or on almost the same level.

Next, functions will be described.

When a user grips Handle 10, and brings Head 20's Contact face 34 with skin into contact with skin applied to by lotion, Electrode 11A and 11B are conductive via a body, ion-introducing function begins, and essence is ionized and infiltrates deeper in skin. At this point, Shaft 35 is pushed down on to the backward position in FIG. 3 by biasing power of Biasing member 36, and fits into Air pocket 33 in Frame 32 with Pad 31.

Figure 4:
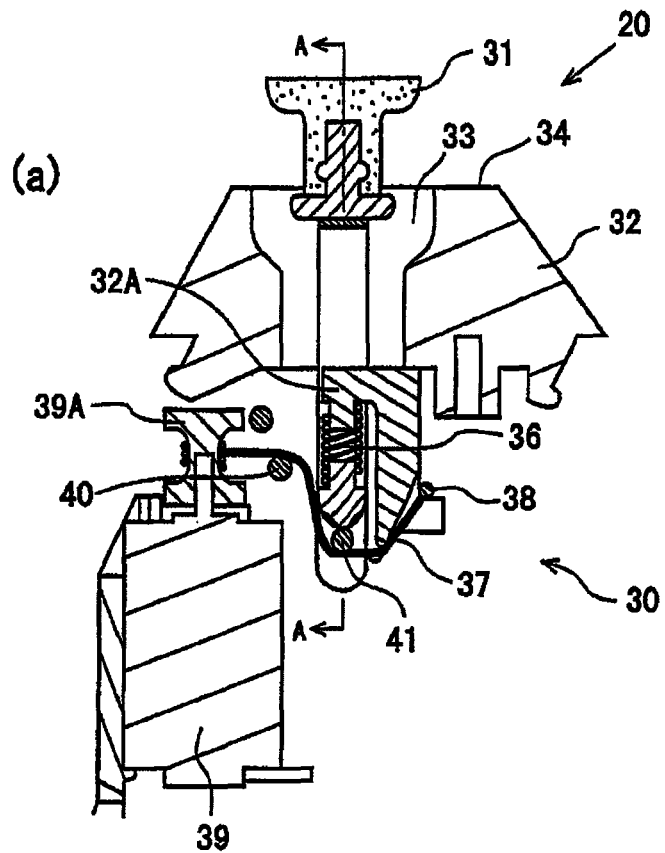
FIG. 4 is also a cross-section view of FIG. 2,
 (a) shows a state that a pad outstands, while
 (b) shows a cross-section surface of the substantial part along A-A line in (a).
Figure 4:
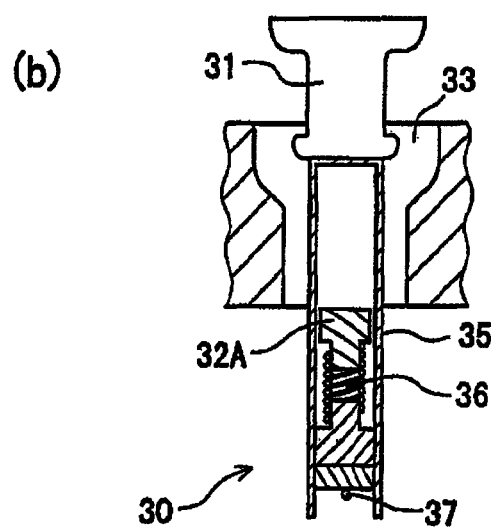

Then, Operating portion 12 is operated, and Actuator 39 starts driving. Actuator 39 reels Wire rod 37 to Take-up axis 39A, and tension is provided on Wire rod 37 between fixed member 38 and Take-up axis 39A. Thus, Wire rod 37 extrudes Shaft 35, as shown in FIG. 4, and Pad 3 protrudes and pats skin with Contact face 34.

When skin is patted, Actuator 39 stops temporarily and tension of Wire rod 37 slacks. Then, as shown in FIG. 3, by biasing power of Biasing member 36, Take-up axis 39 turns back, and Wire rod 37 is uncoiled, Shaft 35 is pushed down, Pad 31 is absorbed in the original position of Air pocket 33 from Contact ace 34 and settles there again. Here, as Actuator 39 is set to drive intermittently, Wire rod 37 in FIGS. 3 and 4 is repeatedly unstrung and reeled, Shaft 35 repeats piston actions, and Pad 31 continuously pats skin.

When Actuator 39 is a motor, switching on and off periodically actualizes piston actions. If it is a direct-current motor, by applying the power brake shunting a supply circuit when the motor is off, it puts a brake on Take-up axis 39A's reverse, preventing ravelments caused by Wire rod 37's rapid winding and unweaving. It is preferable for a period of switching on and off of the power motor to be 10 times per second.

With Tapping mechanism 30 above, not only beneficial effects of massage, effectiveness in relaxation and stimulating an acupuncture point, but in combination with ion-introducing function by Ion-introducing electrode 11A, 11B Tapping mechanism 30's tapping helps active ingredients of essence to infiltrate in the skin coated with essence, and enhances its effectiveness.

And in this applied mode 1, compared to the existing approach with a twist cam, no frictional noise is generated and it is silent, and the shape offers great flexibility. It downsizes Tapping mechanism 30 and saves weight.

Figure 5:
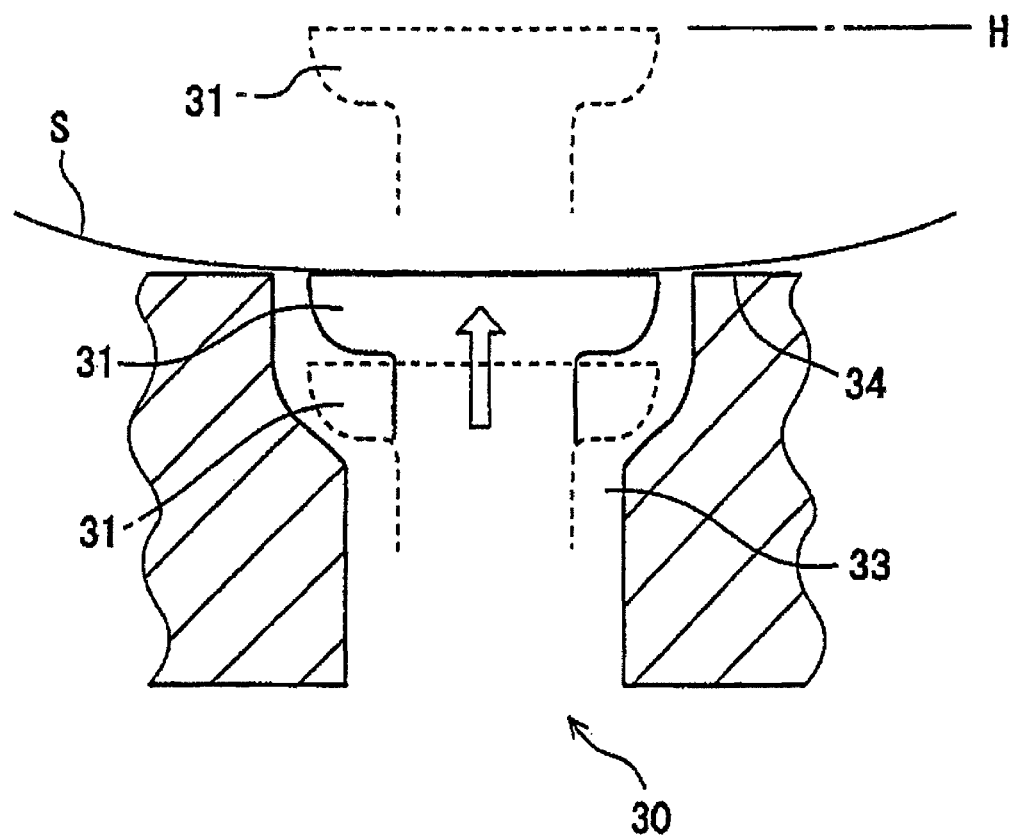
FIG. 5 is an explanatory diagram of functions of the tapping mechanism.

Additionally, as shown in FIG. 5, Tapping mechanism 30 is equipped with Air pocket 33 on the side that Pad 31 is received in from Contact face 34. Shaft 35 can work swiftly toward Skin S in a state that Contact face 34 touches Skin S, and quick and light tapping becomes possible. At this point, energy that Pad 31 reaches to the culmination H when it is not in contact with Skin S, defines the strength of tapping.

In the description above, Shaft 35 is rolled back by the biasing power of Biasing member 36. Also by driving Actuator 39 to reel Wire rod 37, Shaft 35 is made to advance by the force of more than just biasing power (FIG. 6(*a*)). The other way around, the shaft can be advanced by the biasing power of Biasing member 36. Further, by driving Actuator 39 to reel Wire rod 37, Shaft 35 can be rolled back by the force of more than biasing power. In that case, repulsion depending on suppleness and firmness can be absorbed in the Biasing member 36.

Further, although Ion-introducing electrodes 11A, 11B infiltrating essence coat skin by introducing ions, they are not indispensable components, but omissible.

Additionally, as shown in FIG. 1(*b*), Tapping mechanism 30 has more than two exchangeable pads, Pad 31L, 31S (there are two kinds of pads in the drawing, but more than three are acceptable) which are different in dimension, and composed on one side of Shaft 35 for freely being put on and taken off. Further, it is understood that it is possible to modify dimensions of Pad 31 according to user applications or preferences and also to tap variously. For example, pads whose faces are wide like 31L feel soft as strength is dispersed, meanwhile those which are narrow feel hard because of centered strength.

Furthermore, the device for producing beautiful skin does not set limits on the number of Tapping mechanisms 30. That is, it can be equipped with more than two Tapping mechanisms 30 and pat skin facing Contact faces 34, with each Tapping mechanism 30. Through this process, it becomes possible to tap simultaneously more than two parts of skin, and to improve effectiveness of skin care.

Figure 6:
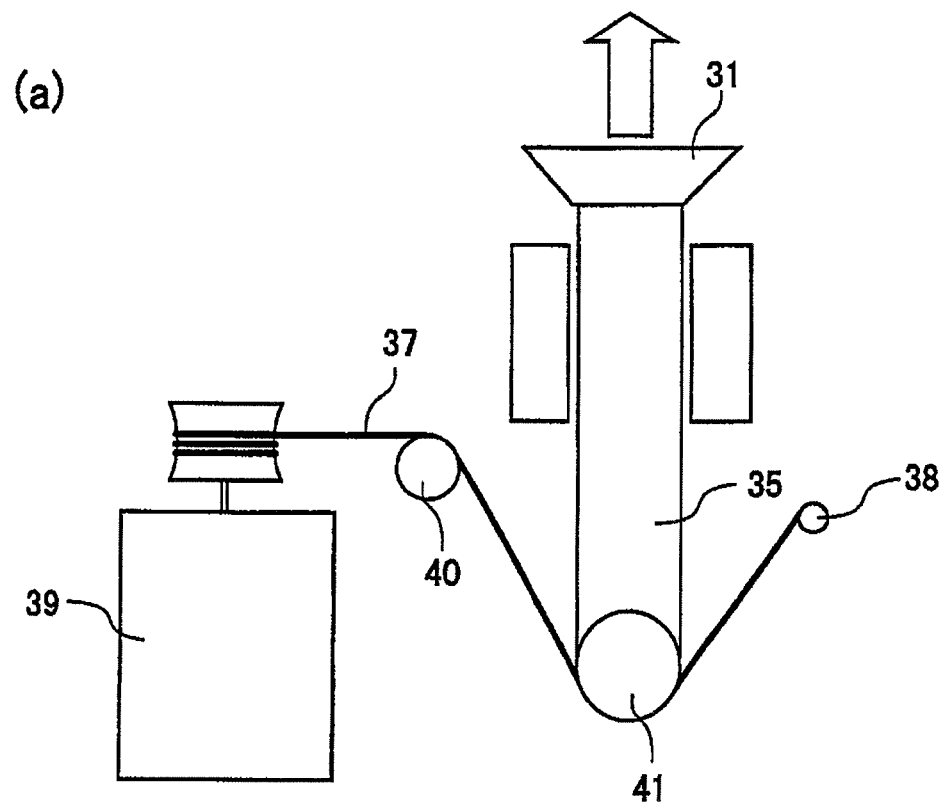
FIG. 6 is a conceptual diagram of the tapping mechanism,
 (a) is an example of [FIG. 2], while
 (b) shows another example.
Figure 6:
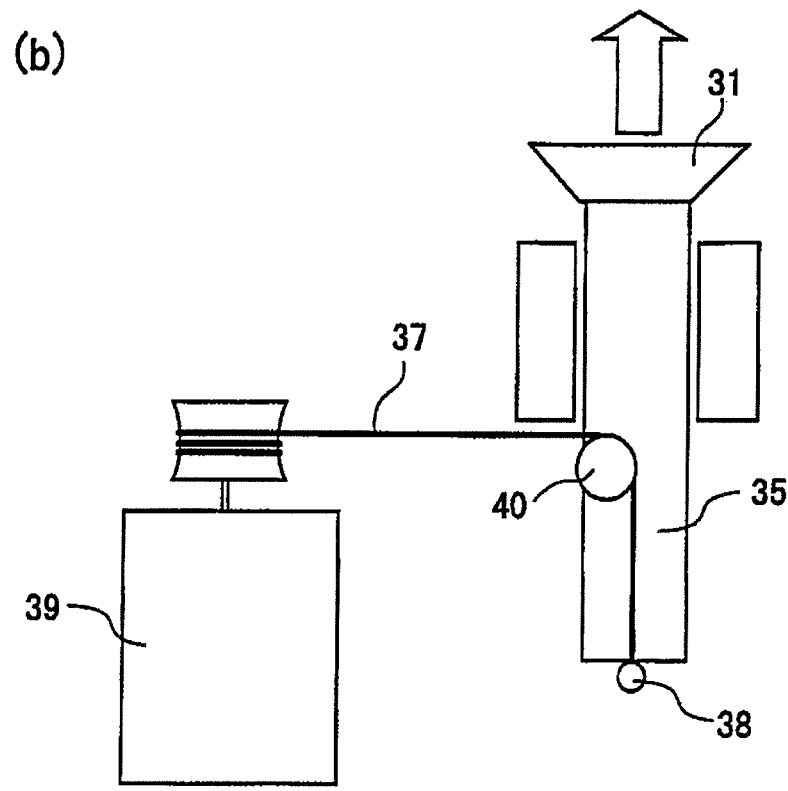

Also, in the description above, with reference to FIG. 6(*a*), it is acceptable to have Fixed member 38 and Pilot pin 40 at both ends of Shaft 35, and pull up Pilot pin 41 under Shaft 35 by reeling Wire rod 37, and in addition to this, with reference to FIG. 6(*b*), it is also acceptable to pull up Pilot pin 41 by Wire rod 37, with Fixed member 38 placed under Shaft 35. As in FIG. 6(*a*), reeling wire rod 37 by 2 cm makes it possible to tap powerfully because Shaft 35 is pulled up by 1 cm on the other hand as in FIG. 6(*b*), reeling Wire rod 37 by 1 cm still makes it possible to tap rapidly because Shaft 35 is also pulled up by 1 cm.

Figure 7A:
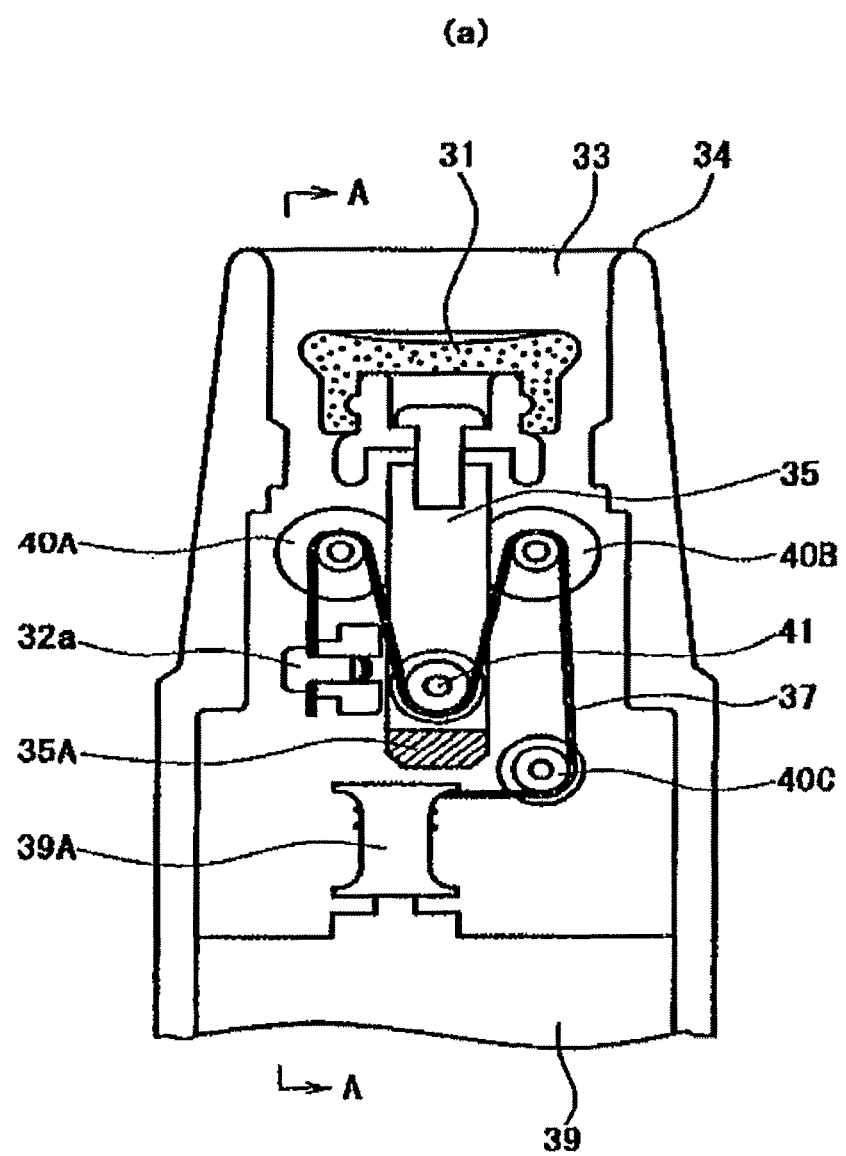
FIG. 7 is another example of a cross-section view of the tapping mechanism,
 (a) shows a state that a pad falls back, while
 (b) is a lateral view which is along A-A line at the time.
Figure 7B:
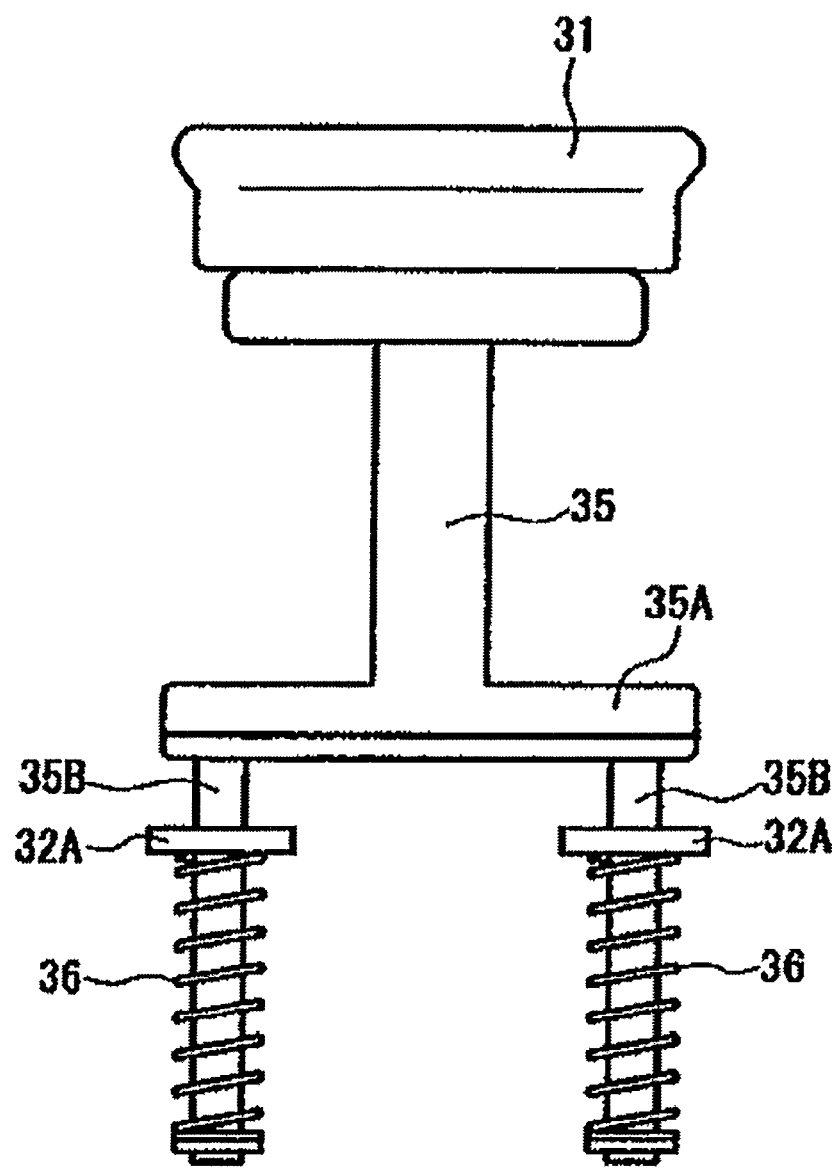
Figure 8A:
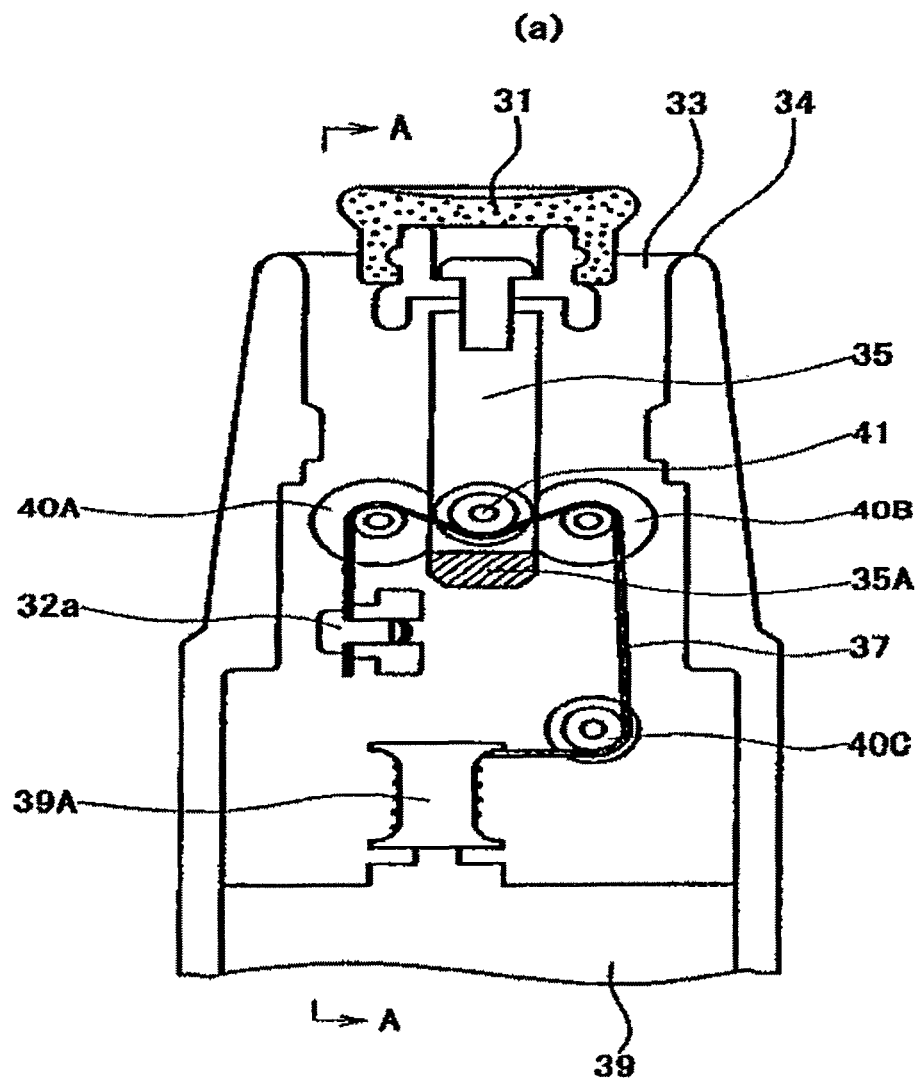
FIG. 8 shows in (a) that the pad in FIG. 7 has advanced, while
 (b) shows a lateral view of the substantial part along A-A line in (a).
Figure 8B:
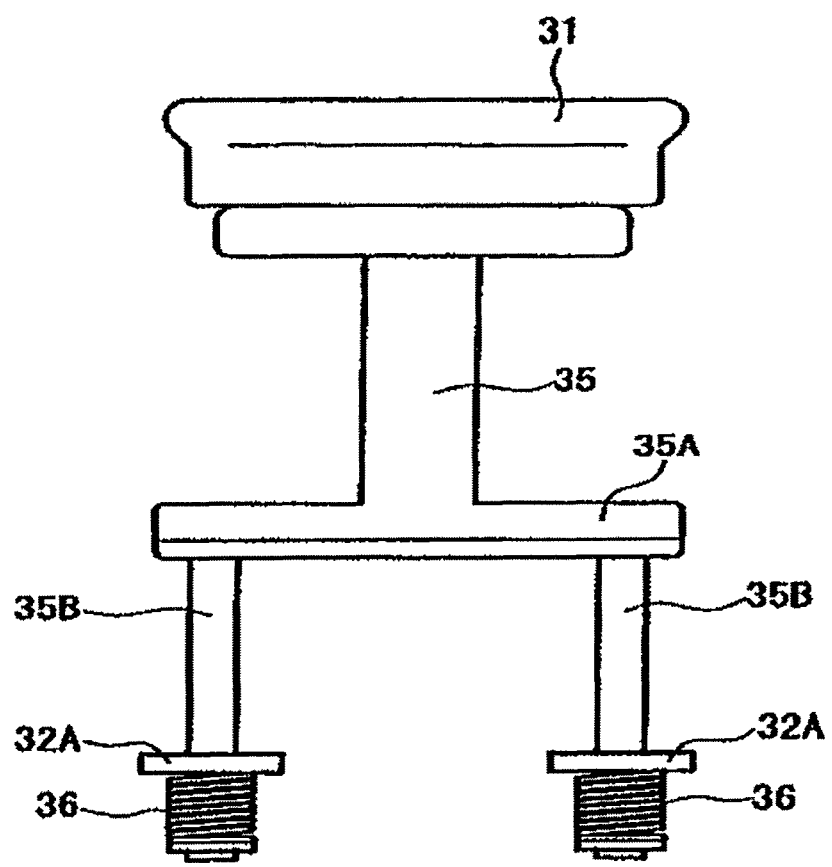

In Embodiment 2 of FIGS. 7 and 8, Fixed pulleys 40A, 40B corresponding to Pilot pin 40 in FIG. 2 are set out on either side of Shaft 35, and the third Fixed pulley 40c is placed next to Take-up axis 39A. One end of Wire rod 37 is fixed to Take-up axis 39A, and the other to Frame 32.

In this case, as shown in FIG. 7, 8(*b*), Shaft 35 sets up Supporting member 35B on either side of Base 35A orthogonal to its rear anchor, and Biasing member 36 is attached thereto. In the drawings, 32A is a locking part integrated with Frame 32, which latches together one end of Biasing member 36. Right-and-left Supporting member 35B slidably penetrates Locking part 32A of the frame, ensuring linear reciprocating motions.

By driving Actuator 39, and reeling Wire rod 37 by Take-up axis 39A, Wire rod 37 tenses and its tension advances Shaft 35 through Pilot pin 41. In this way, Pad 31 pats skin, projecting from Contact face 34 with skin of Head 20.

Here Biasing member 36 is compressed as in FIG. 8 (*b*), when Actuator 39 stops, stored biasing power to roll back Shaft 35 to the original position, and Shaft 35 provides piston actions.

According to this Embodiment 2, Shaft 35 disposes Fixed pulleys 40A, 40B on both sides, and the third Fixed pulley 40C next to Take-up shaft 39A. In addition to the effect that operating sound is tranquil, with Actuator 39 placed beneath Shaft 35, it allows for downsizing further the Tapping mechanism.

Figure 9:
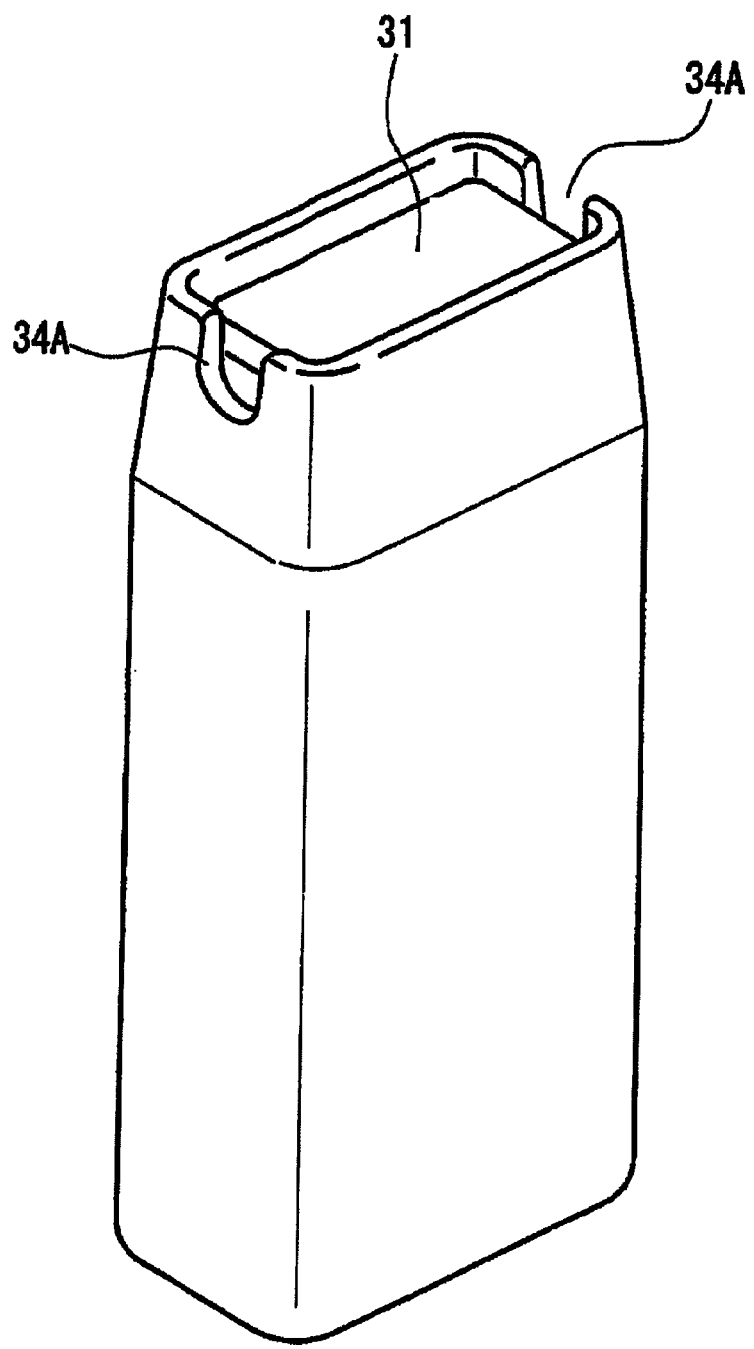
FIG. 9 is a perspective view of a device for producing beautiful skin, which differs from FIG. 1 in morphology.

FIG. 9 is an example where the surface of Pad 31 is formed on a concave cupule, which is capable of pushing or pulling up skin.

Figure 10:
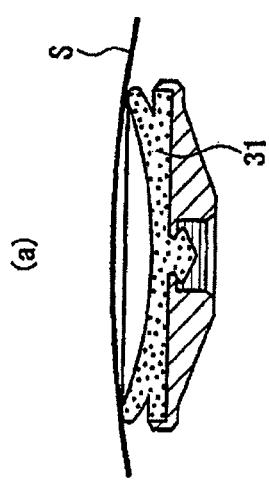
FIG. 10 is an explanatory diagram of functions of the device in FIG. 9,
 (a) shows that a state that a pad outstands and pats skin,
 (b) shows that a state that a pad is absorbed to skin, while
 (c) shows a state that a pad draws up skin.
Figure 10:
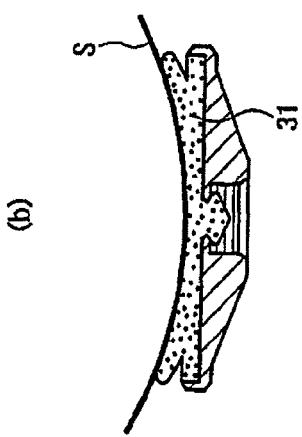
Figure 10:
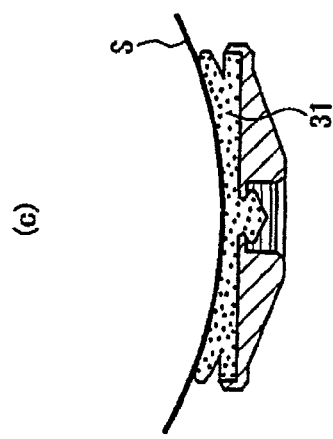

To explain the function in FIG. 10, firstly Pad 31 pushes skin and transforms it into an almost flat figure (a), and the pad is brought into a state compressed against skin (b). Then Pad 31 rolls back to pull up Skin S compressed as in (c). Repeating this process stimulates blood circulation.

Finally, item 34A in FIG. 9 is a concave formed in Contact face 34, by putting a finger here enables Pad 31 to be easily replaced by pinching.

EXPLANATION OF SYMBOLS

10 Handle
11A Ion-introducing electrode (to contact with skin)
11B Ion-introducing electrode (to contact with palms)
12 Operating portion
13 Display
20 Head
30 Tapping mechanism
31, 31L, 31S Pad
32 Frame
33 Air pocket
34 Contact face with skin
35 Shaft
37 Wire rod
38 Fixed member
39 Actuator
39A Take-up axis
40, 41 Pilot pin
S Skin

What is claimed is:

1. A tapping device for cosmetic skin care, comprising:
a head for contacting a skin;
a tapping mechanism including a pad for patting the skin facing the head, and a shaft, wherein the pad is connected to an end of the shaft, the pad being adapted to be projected from and retracted into the head by a linear movement;
a biasing member that biases the shaft towards one direction of the linear movement;
a wire rod that empowers the shaft against a biasing force of the biasing member when tension is applied thereto; and
an actuator that applies tension intermittently to the wire rod.

2. The device as in claim 1, wherein said head comprises an electrode infiltrating essence for introducing ions.

3. The device as in claim 1, wherein the tapping mechanism has a space between a surface of the head and a back portion of the pad.

4. The device as in claim 1, wherein the tapping mechanism comprises more than two exchangeable pads which are different in dimensions, and placed on one side of the shaft for freely being put on and taken off.

5. The device as in claim 1, wherein the pad comprises a surface that is a concavely curved cupule.

\* \* \* \* \*